(12) United States Patent
Kim et al.

(10) Patent No.: US 8,481,301 B2
(45) Date of Patent: Jul. 9, 2013

(54) CENTRIFUGAL MICRO-FLUIDIC STRUCTURE FOR MEASURING GLYCATED HEMOGLOBIN, CENTRIFUGAL MICRO-FLUIDIC DEVICE FOR MEASURING GLYCATED HEMOGLOBIN, AND METHOD FOR MEASURING GLYCATED HEMOGLOBIN

(75) Inventors: In Wook Kim, Seongnam-si (KR); Na Hui Kim, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 194 days.

(21) Appl. No.: 12/883,786

(22) Filed: Sep. 16, 2010

(65) Prior Publication Data
US 2011/0143364 A1 Jun. 16, 2011

(30) Foreign Application Priority Data
Dec. 10, 2009 (KR) .................. 10-2009-0122227

(51) Int. Cl.
*C12M 1/34* (2006.01)
(52) U.S. Cl.
USPC ................ 435/287.1; 435/286.5; 436/524
(58) Field of Classification Search
None
See application file for complete search history.

(56) References Cited

U.S. PATENT DOCUMENTS

| | | | |
|---|---|---|---|
| 4,721,681 A * | 1/1988 | Lentrichia et al. | 436/523 |
| 5,674,699 A * | 10/1997 | Saunders et al. | 435/7.93 |
| 6,174,734 B1 * | 1/2001 | Ito et al. | 436/518 |
| 2002/0137218 A1 * | 9/2002 | Mian et al. | 436/45 |
| 2003/0102215 A1 * | 6/2003 | Bukshpan et al. | 204/459 |
| 2004/0089616 A1 | 5/2004 | Kellogg et al. | |
| 2005/0014249 A1 * | 1/2005 | Staimer et al. | 435/287.2 |
| 2007/0099301 A1 | 5/2007 | Tyvoll et al. | |
| 2008/0056949 A1 | 3/2008 | Lee et al. | |
| 2008/0108120 A1 | 5/2008 | Cho et al. | |

FOREIGN PATENT DOCUMENTS

| | | |
|---|---|---|
| KR | 10-2008-0005224 A | 1/2008 |
| KR | 10-0883658 A | 2/2009 |

OTHER PUBLICATIONS

Little et al., A review of variant hemoglobins interfering with hemoglobin A1c measurement, May 2009, J Diabetes Science and Tech, 3(3): pp. 446-451.*

International Searching Authority, International Search Report, issued Jul. 19, 2011, in counterpart PCT application No. PCT/KR2010008261.

The European Patent Office, Communication, dated Apr. 17, 2013, issued in counterpart European Patent Application No. 10836152.8.

* cited by examiner

*Primary Examiner* — N. C. Yang
(74) *Attorney, Agent, or Firm* — Sughrue Mion, PLLC

(57) ABSTRACT

Disclosed are a centrifugal micro-fluidic structure for measuring glycated hemoglobin, a centrifugal micro-fluidic device for measuring glycated hemoglobin, and a method for measuring glycated hemoglobin. According to the disclosure, immunosorbent assay and affinity measurements are simultaneously conducted using only a single device in order to detect hemoglobin variants or interfering substances and, therefore, the detected results are applied to analysis of measurement results so as to eliminate and/or compensate for, or calibrate errors in measurement of, glycated hemoglobin, thereby more accurately measuring the glycated hemoglobin.

13 Claims, 6 Drawing Sheets

CENTRIFUGAL MICRO-FLUIDIC STRUCTURE FOR MEASURING GLYCATED HEMOGLOBIN, CENTRIFUGAL MICRO-FLUIDIC DEVICE FOR MEASURING GLYCATED HEMOGLOBIN, AND METHOD FOR MEASURING GLYCATED HEMOGLOBIN

CROSS-REFERENCE TO RELATED APPLICATION

This application claims the priority of Korean Patent Application No. 2009-122227 filed on Dec. 10, 2009 with the Korean Intellectual Property Office, the disclosure of which is incorporated herein by reference.

BACKGROUND

1. Field

Embodiments of the present invention relate to a centrifugal micro-fluidic structure for measuring glycated hemoglobin, a centrifugal micro-fluidic device for measuring glycated hemoglobin, and a method for measuring glycated hemoglobin. More particularly, embodiments relate to a micro-fluidic structure wherein only one device simultaneously conducts an immunosorbent assay and affinity chromatography measurements, which are particularly selected from various methods for determining glycated hemoglobin, so as to detect hemoglobin variants or interfering substances. The detected results are applied to analysis of measurement results in order to eliminate and/or compensate for, or calibrate errors in measurement of, glycated hemoglobin, thereby more accurately determining the glycated hemoglobin. A centrifugal micro-fluidic device for measuring glycated hemoglobin which includes the foregoing structure, and a method for measuring glycated hemoglobin using the same are also disclosed.

2. Description of the Related Art

In order to flow and move a fluid in a micro-fluidic structure, a driving pressure is generally required. As such a driving pressure, capillary pressure or pressure generated using an additional pump may be used. In recent years, clinical diagnostic analyzers designed to enable a detection of a target material present in a small amount of fluid in simple and economical ways including, for example, a centrifugal micro-fluidic device having a micro-fluidic structure mounted on a circular disk type rotational platform such as lab-on-a disk and/or a lab CD have been proposed.

Lab-on-a disk meaning 'laboratory on a disk' is a CD type device in which various components are integrated for analysis of biomolecules used in a laboratory. Upon introducing a biological sample such as blood to the micro-fluidic structure of the disk, a fluid such as a sample, a chemical reagent, etc. may be transferred to a desired location simply by applying centrifugal force without additional driving systems such as driving pressure in order to transport the fluid.

Glycated hemoglobin, or glycosylated hemoglobin, or hemoglobin A1c (hereinafter, sometimes referred to as 'HbA1c') has been recognized to be a useful tool for screening for diabetes, checking blood sugar control in people who might be pre-diabetic, or monitoring blood sugar control in patients with diagnosing diabetes mellitus. In the normal 120-day lifespan of the red blood cell, glucose molecules react with hemoglobin, forming glycated hemoglobin. Once a hemoglobin molecule is glycated, it remains that way. A buildup of glycated hemoglobin within the red cell, therefore, reflects the average level of glucose to which the cell has been exposed during its life-cycle. Measuring glycated hemoglobin may assess the effectiveness of therapy of diabetes by monitoring long-term serum glucose regulation. The $HbA_{1c}$ level is proportional to average blood glucose concentration over the previous four weeks to three months.

It has been reported that glycation of hemoglobin has been associated with cardiovascular disease, nephropathy, and retinopathy in diabetes mellitus. Monitoring the HbA1c in type-1 diabetic patients may improve treatment.

When an emergency outpatient testing is required for HbA1c level, the testing should be performed, from starting the test to reporting a result of the test, within 30 minutes and, according to results thereof, further courses of action are determined. Therefore, a rapid and accurate test is required.

At present, a number of test instruments for measuring glycated hemoglobin are commercially available and widely used in the art. These conventional methods for measuring glycated hemoglobin, employ either boronate affinity measurement or immuno-agglutination assay based measurement. The boronate affinity measurement method uses an isolation of glycated hemoglobin from unglycated hemoglobin by a mechanism wherein boronic acid binds to cis-diol of saccharide. The immuno-agglutination assay-based measurement method uses agglutination of an antigen-antibody complex using an antibody specific for the glycated hemoglobin.

However, the foregoing methods have a common drawback of inevitable errors caused by inherent characteristics of each of the methods. For example, in the boronate affinity measurement method, the boronate may be cross-linked with other components receiving cis-diol groups present in blood, thus causing a false decrease in the measured glycated hemoglobin value. On the other hand, the immuno-agglutination method cannot detect hemoglobin variants such as HbF, HbS, HbC, etc., which in turn may cause a false decrease in the measured glycated hemoglobin value.

Consequently, depending on the kinds of hemoglobin variants and/or the measurement methods employed, HbA1c measurement results do not always accurately match clinical status related thereto. Therefore, although both of the foregoing measurement methods must be employed together in order to more precisely determine HbA1c, these methods entail technical difficulties in embodying both of them in a single device since the methods are based on different measurement principles.

Accordingly, there is still a requirement for developing a novel measurement method to overcome the above cited technical restrictions.

SUMMARY

An exemplary embodiment provides a centrifugal micro-fluidic structure for more accurately measuring the glycated hemoglobin level in a biological sample, wherein a single device simultaneously conducts an immunosorbent assay and an affinity chromatography measurement, which are particularly selected for detecting not only glycated hemoglobin, but also glycated hemoglobin variants or interfering substances. The detected results are applied to analysis of measurement results in order to eliminate and/or compensate for, or calibrate errors in measurement of glycated hemoglobin, thereby rendering a more accurate detection of glycated hemoglobin level. In addition, a centrifugal micro-fluidic device for measuring glycated hemoglobin which includes a rotational body as well as the centrifugal micro-fluidic structure described above is also provided.

According to an aspect of the present invention, there is provided a centrifugal micro-fluidic structure, including: a plurality of chambers; channels through which the chambers are connected to one another; and valves for opening and closing the channels, wherein the structure also has separate chambers to contain at least two different glycated hemoglobin affinitive particles, respectively, and a control chamber.

One type of the HbA1c particles has an antibody selectively binding to HbA1c fixed to a surface thereof, while the other type may have boronic acid, boronate or a boronate derivative binding to a cis-diol group in HbA1c fixed to a surface thereof.

The HbA1c affinitive particles may be combined with a solid support having a specific gravity sufficient to enable a homogeneous mixing of HbA1c particles with HbA1c in a blood sample and/or precipitation of the bound HbA1c particles under centrifugal force. In an embodiment, such solid support may have a specific gravity of 1.3-2.0, and may be made of a material selected from, 2-12% cross linked agarose, galactose polysaccharide and polyacrylamide gel.

The antibody described above may be a monoclonal antibody or a polyclonal antibody.

The micro-fluidic structure may further include a sedimentation chamber connected to each of the separate chambers containing HbA1c affinitive particles and such sedimentation chamber may receive HbA1c combined with the HbA1c affinitive particles which were precipitated by centrifugal force.

The micro-fluidic structure may also include a detection chamber connected to each of the control chamber and the separate chambers in which HbA1c affinitive particles are contained, respectively.

The separate chambers in which HbA1c affinitive particles are contained, respectively, and the control chamber may be located at equal intervals around a rotational center in radial direction.

According to another aspect of the present invention, there is provided a centrifugal micro-fluidic device, including a rotational body, at least one micro-fluidic structure and a detection unit, wherein the micro-fluidic structure includes: a plurality of chambers; channels through which the chambers are connected to one another; and valves for opening and closing the channels, wherein the micro-fluidic structure also has separate chambers to contain at least two different glycated hemoglobin affinitive particles, respectively, and a control chamber, and wherein a fluid contained in the micro-fluidic structure is transported using centrifugal force generated by rotation of the rotational body.

The detection unit has an optical system emitting monochromatic light and the optical system may determine absorbance of each of first to third detection chambers using light with a wavelength ranging from 400 to 600 nm.

According to a still another embodiment, there is provided a method for measuring HbA1c using the centrifugal micro-fluidic device described above, including: providing a device including a first receiving chamber which contains one type of HbA1c particles to which an antibody selectively binding to HbA1c is fixed, and a second receiving chamber which contains another type of HbA1c particles to which boronic acid, boronate or a boronate derivative binding to a cis-diol group in HbA1c is fixed; conducting hemolysis of a blood sample injected into the micro-fluidic device; introducing a pre-metered volume of the hemolyzed blood sample into each of first and second receiving chambers (hereinafter, abbreviated as 'first and second chambers') as well as a control chamber; combining the hemolyzed blood sample with the particles contained in the first and second chambers, respectively; precipitating HbA1c bound to the particles under centrifugal force to give a supernatant in the respective chambers; measuring absorbance of each of the supernatants in the first and second chambers as well as the control chamber; calculating a first absorbance ratio with respect to antibody according to the following Equation 1, then, estimating a first HbA1c level (%) from a standard calibration curve with respect to antibody; calculating a second absorbance ratio with respect to boronate affinity according to the following Equation 2, then, estimating a second HbA1c level (%) from another standard calibration curve with respect to boronate affinity; and comparing the first HbA1c level (%) with the second HbA1c level (%).

first absorbance ratio={(absorbance of supernatant in control chamber−absorbance of supernatant in first chamber)/absorbance of supernatant in control chamber}  Equation 1:

second absorbance ratio={(absorbance of supernatant in control chamber−absorbance of supernatant in second chamber)/absorbance of supernatant in control chamber}  Equation 2:

The foregoing method may further include providing information for existence of hemoglobin variants in a blood sample when the first HbA1c level (%) is less than the second HbA1c level (%).

Alternatively, the forgoing method may further include providing information for existence of interfering substances having cis-diol groups in a blood sample when the first HbA1c level (%) is greater than the second HbA1c level (%).

In this regard, precipitation of bound HbA1c may be conducted in sedimentation chambers connected to the first and second chambers, respectively.

Measurement of absorbance may be performed after transporting the fluid into separate detection chambers connected to the control chamber and the first and second chambers, respectively.

Also, absorbance may be measured using light with a wavelength ranging from 400 to 600 nm.

In such method, a washing process for removal of unreacted and/or non-reactive materials may be carried out between respective processes.

BRIEF DESCRIPTION OF THE DRAWINGS

The above and other embodiments will become apparent and more readily appreciated from the following descriptions, taken in conjunction with the accompanying drawings of which.

DETAILED DESCRIPTION

Hereinafter, advantageous features and characteristics and practical methods will be clearly understood through the following detailed description of embodiments with reference to the accompanying drawings. However, at least one exemplary embodiment may be embodied in various other forms, which are not particularly restricted to those described herein.

A micro-fluidic structure for measuring glycated hemoglobin and a centrifugal micro-fluidic device having the same are characterized in that a single device simultaneously conducts both the immunosorbent assay and boronate affinity measurements based on a structural difference between hemoglobin molecules, so as to measure the glycated hemoglobin and to detect hemoglobin variants.

According to an aspect, a centrifugal micro-fluidic structure includes: a plurality of chambers; channels through which the chambers are connected to one another; and valves for opening and closing the channels, wherein the structure also has at least two separate chambers each containing different HbA1c affinitive particles from other chambers, and a control chamber.

Figure 1:
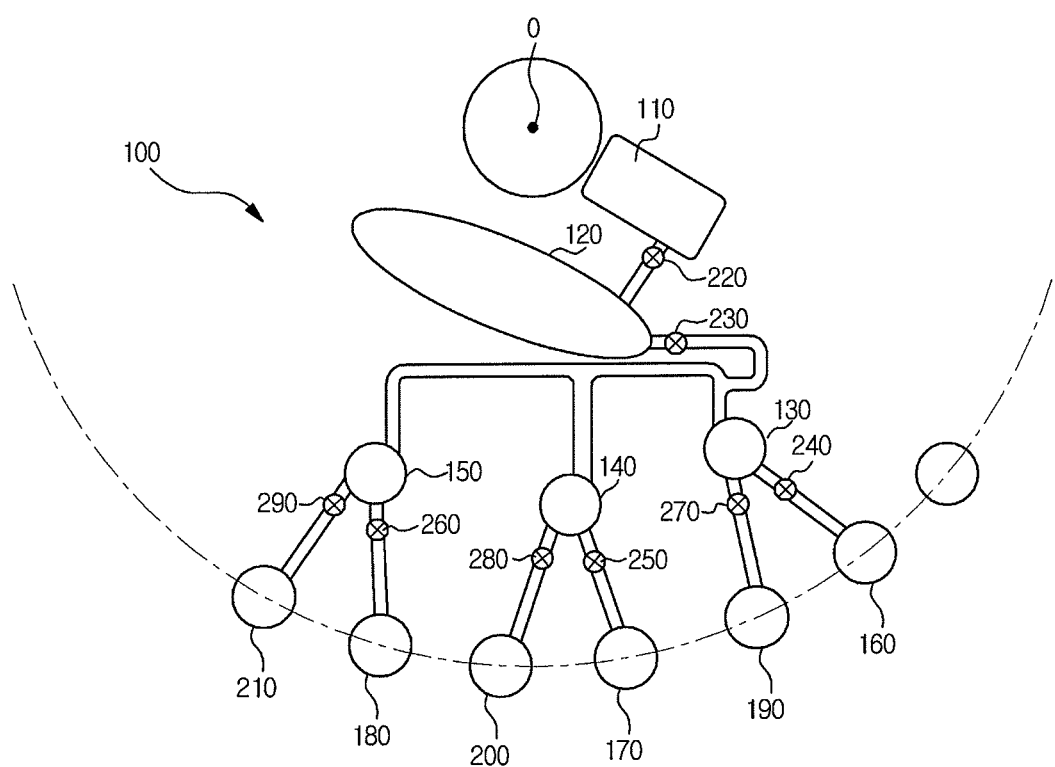
FIG. 1 is a schematic view illustrating a structure of a micro-fluidic device according to an exemplary embodiment.

FIG. 1 is a schematic view illustrating a structure of a micro-fluidic device according to an aspect.

That is, FIG. 1 shows a configuration of an exemplary embodiment of the inventive micro-fluidic device, comprising: a chamber 120 in which various analytical buffers are stored; separate chambers for conducting biological and/or chemical reactions; a sample chamber 110 containing a blood sample; fluid channels through which treated fluids and the buffers are transported; and valves for opening and closing the fluid channels.

Referring to FIG. 1, a rotational body used in the exemplary embodiment may comprise a circular disk type platform. However, a shape of the rotational body is not particularly limited thereto. Such a platform is easily fabricated and a surface of the platform may be formed using biologically inactive acryl or other plastic materials. However, a raw material for fabrication of the rotational body is not particularly limited and may include any materials with chemical or biological stability, optical transparency and/or mechanical workability.

One or plural micro-fluidic structures may be provided on the platform. For instance, after partitioning the platform into several sections, separate micro-fluidic structures may be placed independently of one another on the sections, respectively.

The rotational body may be fabricated using at least one selected from a variety of materials such as plastic, polymethylmethacrylate (PMMA), glass, mica, silica, or a silica wafer material. Preferably, the plastic material is used in view of economic merits and simple workability. Potential plastic materials may include polypropylene, polyacrylate, polyvinylalcohol, polyethylene, polymethylmethacrylate, polycarbonate, etc. Polypropylene and polycarbonate are preferably used and polycarbonate is more preferably used.

A blood sample, a blood sample mixture, a buffer solution, a reactive solution, etc. may be transported into the separate chambers using centrifugal force generated by rotation of the rotational body.

A micro-fluidic structure 100 may be located on the rotational body, and may include: a sample chamber 110; a buffer chamber 120 that contains a buffer for separating hemoglobins from a sample, for example hemolysis of a blood sample; first and second chambers 130 and 140 into which the blood samples hemolyzed in the buffer chamber are injected in pre-metered volumes, as well as a control chamber 150; first to third sedimentation chambers 160, 170 and 180 connected to the first and second chambers 130 and 140 and the control chamber 150, respectively, each of which contains a part of the hemolyzed blood samples precipitated by centrifugal force; first to third detection chambers 190, 200 and 210 connected to the first and second chambers 130 and 140 and the control chamber 150, respectively, each of which contains each supernatant of the first and second chambers 130 and 140 and the control chamber 150; channels for connecting the chambers; and valves for opening and closing the chambers.

A valve 220 may be located between the sample chamber 110 and the buffer chamber 120. The valve 220 controls flow of the blood sample in the channel between the sample chamber 110 and the buffer chamber 120. The valve may be any one selected from different types of micro-fluidic valves. The valve 220 may comprise, for example, a normally closed valve wherein a channel of the valve is closed to prevent a fluid from flowing unless the valve opens by external power.

The buffer chamber 120 receives a red blood cell lysis buffer for hemolysis of the blood sample contained in the sample chamber 110. The lysis buffer may include a red blood cell lysis agent generally used in the art. For example, it may include 20 mM HEPES (N-2-hydroxyethylpiperazine-N'-2-ethane sulfonic acid; pH 8.1) as a buffer solution containing a surfactant; a red blood cell buffer solution prepared of 10 ml of 1M Tris (pH 7.6), 5 ml of $MgCl_2$, 10 m of NaCl and 975 ml of distilled water, and so forth. The hemolyzed blood sample contains other blood cell and plasma ingredients such as white blood cells, platelets, etc., in addition to hemoglobin and glycated hemoglobin.

The hemolyzed blood sample is introduced from the buffer chamber 120 to the first and second chambers 130 and 140 as well as the control chamber 150 in a constantly metered volume.

In order to inject the metered volume of blood samples into the first and second chambers 130 and 140 as well as the control chamber 150, parameters such as a running distance of each hemolyzed blood sample between the buffer chamber 120 and each of the chambers 130 to 150 are controlled which in turn enables simultaneous injection of the same volume of blood sample into each of the chambers 130 to 150 in a rotational body with a uniformly accelerated circular motion.

Figure 2:
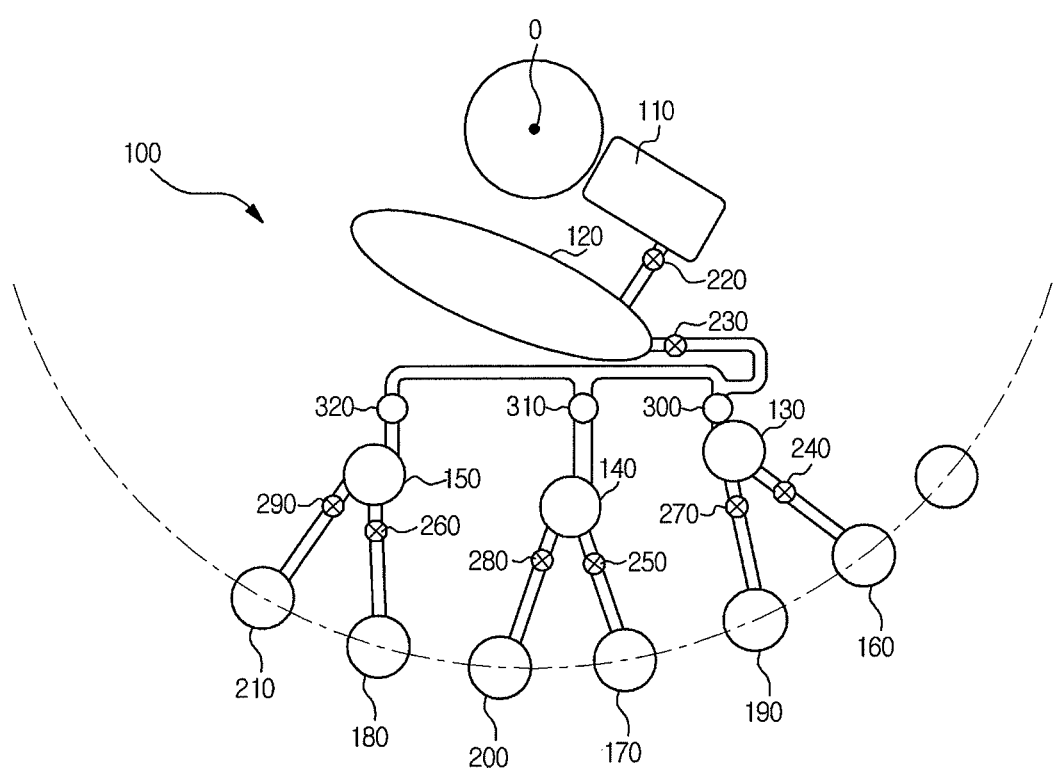
FIG. 2 is a schematic view illustrating a structure of a micro-fluidic device according to another exemplary.

As shown in FIG. 2 illustrating another exemplary embodiment, the micro-fluidic structure includes metering chambers 300, 310 and 320 may be placed between the buffer chamber 120 and each of the first and second chambers 130 and 140 and the control chamber 150, respectively, in order to inject equal volumes of blood samples. Each of the metering chambers 300 to 320 has a volume sufficient to receive a desirable amount of the hemolyzed blood sample required for a measurement. Here, a valve for controlling a flow of the hemolyzed blood sample is fixed to an output of each of the metering chambers 300 to 320. Such a valve may be a normally closed valve identical to the valve 220 described above with respect to FIG. 1. The metering chambers 300 to 320 are respectively connected to the first and second chambers 130 and 140 as well as the control chamber 150 through channels.

The first chamber 120 contains first HbA1c affinitive particles while the second chamber 130 contains second HbA1c affinitive particles, wherein these affinitive particles are bound to HbA1c in the hemolyzed blood sample.

The first and second HbA1c affinitive particles may be coupled with a solid support having a specific gravity sufficient to enhancing thorough mixing of HbA1c particles and HbA1c or precipitation of the resulting bound HbA1c (i.e., HbA1c bound to the particles) by centrifugal force.

Such a solid phase may include, for example, micro particles, magnetic particles, tubes, etc. without particular limitation thereto. The solid phase may be formed using agarose, cellulose, sepharose, polystyrene, polymethylmethacrylate (PMMA), polyvinyl toluene, polyacrylamide, latex, silica, glass, and the like, however, a material of the solid phase is not particularly restricted so long as the material has a specific gravity sufficient to enable a mixing of HbA1c particles with HbA1c and/or precipitation of the resulting bound HbA1c (i.e., HbA1c bound to the particles).

The first and second HbA1c affinitive particles may have hydrophilic surface properties. Because of hydrophilic surface properties, hemoglobins in the hemolyzed blood sample are easily bound to the first and second HbA1c affinitive particles. The solid phase may be made from a material having hydrophilic functional groups including, for example, aldehyde, aliphatic amine, aromatic amine, amide, carboxylic acid, sulfhydryl, chloromethyl, epoxy, hydrazide, hydroxyl, etc. Alternatively, the surface of the solid phase may be treated to have hydrophilic surface properties.

The first and second HbA1c affinitive particles may be present in a liquid or dried state in the chambers. For the liquid state, a concentration of each of the first and second HbA1c affinitive particles may range from 0.01 to 10 wt. %.

An HbA1c affinitive particle may have a size of not more than 1/10 a diameter of a channel connecting chambers. Since the channel generally has a diameter of 50 to 500 μm, a diameter of the HbA1c affinitive particle may range from 5 to 50 μm.

More particularly, the first HbA1c affinitive particles may have an antibody immobilized to a surface of the particles, wherein the antibody selectively binds to HbA1c.

The antibody may be selected from a monoclonal antibody, a polyclonal antibody and an antibody fragment having antigen binding site or complementarity determining region (CDR).

The second HbA1c affinitive particles may include boronic acid, boronate or a boronate derivative fixed to a surface of the particles, wherein such boronic acid, a boronate or a boronate derivative binds to a cis-diol group of HbA1c. Examples of boronate or boronate derivative may be selected from 4-carboxyphenyl boronic acid, 3-nitro-5-carboxy phenyl boronic acid, m-aminophenyl boronic acid, 4-mercaptophenyl boronic acid, thiophene-3-boronic acid, phenyl boronic acid terminated alkane thiol, etc. without particular limitation thereto.

Glycated hemoglobin has cis-diols bound to two β-chains, respectively, wherein glucose is covalently bound to a β-chain based valine terminated amine. A boronate moiety such as boronic acid, a boronate or a boronate derivative binds to the cis-diol group.

To enable the first and second HbA1c affinitive particles contained in the first and second chambers to bind to HbA1c in the hemolyzed blood sample, the hemolyzed blood sample is brought to be in contact with the first and second HbA1c affinitive particles for a sufficient period of time, for example from 3 to 15 minutes. Then the bound HbA1c (i.e., a complex of HbA1c and the first HbA1c affinitive particle, and a complex of HbA1c and the second HbA1c affinitive particle) in the first and second chambers 130 and 140 is precipitated into the first and second sedimentation chambers 160 and 170, respectively, by rotating the micro-fluidic structure. Here, after opening valves 240 and 250 mounted on first outlets of the first and second chambers, the micro-fluidic device undergoes rotation. The third chamber (control chamber) 150 contains only hyemolyzed blood sample, and thus no precipitation of bound HbA1c occurs.

According to another embodiment, when bound HbA1c is precipitated from the first and second chambers 130 and 140 to the first and second sedimentation chambers 160 and 170, other blood components with a specific gravity higher than hemoglobin, for example white blood cells present in the hemolyzed blood sample, may be precipitated from the control chamber 150 to a third sedimentation chamber 180. Further sedimentation of such components may be performed in order to more precisely determine the absorbance of the total hemoglobin in the hemolyzed blood sample which is not brought into contact with an antibody or a boronate moiety.

In this case, the first to third sedimentation chambers 160 to 180 may be located at equal intervals around a rotational center in a radial direction.

After completing precipitation of HbA1c bound to HbA1c affinitive particles from the first and second chambers 130 and 140 to the first and second sedimentation chambers 160 and 170, the valves 240 and 250 and, if necessary, a valve 260 are closed to stop flow of the fluid. Each valve 240 to 260 may be a normally closed valve identical to the foregoing valve 220.

Afterward, each supernatant of the first and second chambers 130 and 140 and the control chamber 150 is transported into each of the first to third detection chambers 190, 200 and 210, in order to determine the concentration of hemoglobin including hemoglobin and free HbA1c contained in the respective supernatants. More particularly, after opening valves 270, 280 and 290 mounted on second outlets of the first and second chambers 130 and 140 and the control chamber 150, the micro-fluidic structure undergoes rotation. Alternatively, the micro-fluidic structure may rotate simultaneously with opening the valves or, otherwise, after rotating the micro-fluidic structure, the valves may be opened. The first to third detection chambers 190, 200 and 210 may be located at equal intervals from the rotational center in a radial direction.

The transported supernatant is subjected to measurement of absorbance in the first to third detection chambers 190, 200 and 210.

Figure 3:
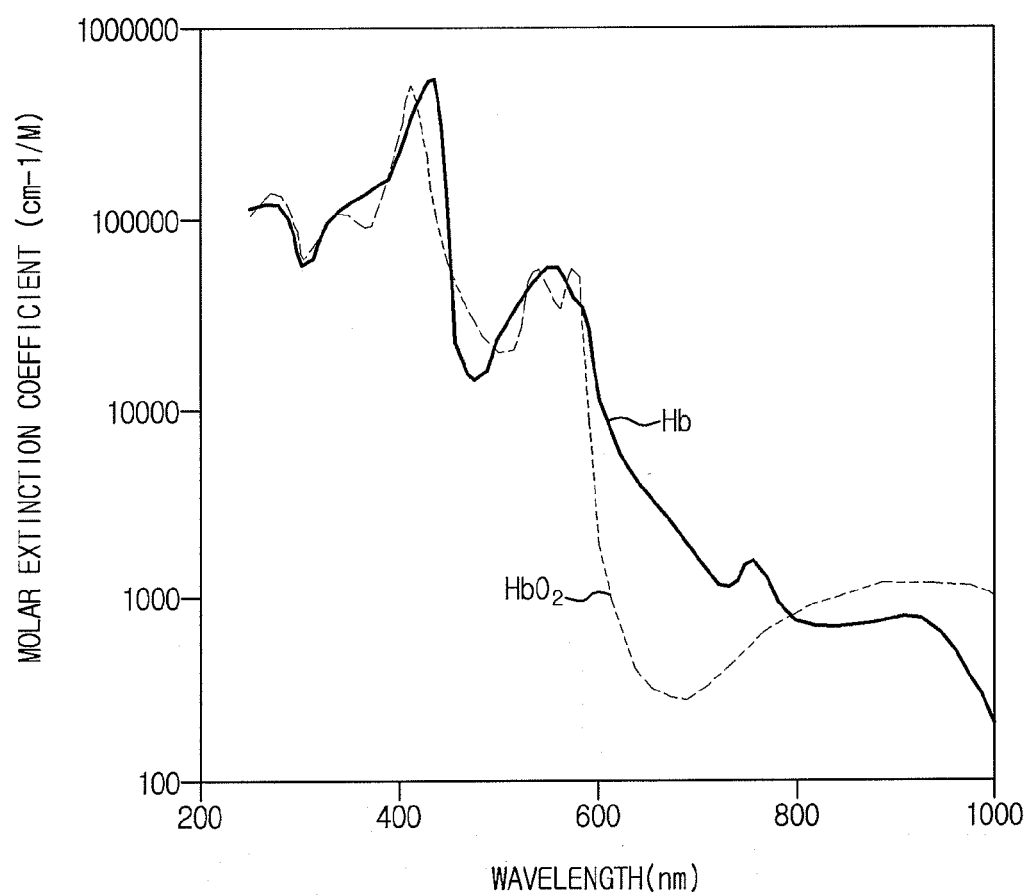
FIG. 3 is a graph showing a relationship between molar extinction coefficient of hemoglobin and light wavelength.

FIG. 3 is a graph showing a relationship between molar extinction coefficient of hemoglobin and light wavelength. As shown in FIG. 3, using light at 400 to 600 nm absorbed by hemoglobin, absorbance of the hemoglobin is measured. The absorbance at 400-600 nm by hemoglobin is an indicator of the level of hemoglobin contained in the tested sample, regardless whether hemoglobin is glycated or not. Thus, when the sample contains both hemoglobin and glycated hemoglobin, the absorbance is proportional to the concentration of the total amount of the hemoglobin and the glycated hemoglobin.

More particularly, a decrease in the concentration of hemoglobin due to precipitation of HbAc1 bound to antibody is determined in the first detection chamber 190 while a decrease in concentration of hemoglobin due to precipitation of HbAc1 bound to boronate moiety is determined in the second detection chamber 200. A concentration of whole hemoglobin is measured in the third chamber 210.

Briefly, absorbance A1 exhibiting a decrease in the concentration of hemoglobin with respect to antibody binding is obtained in the first detection chamber 190, while absorbance A2 exhibiting a decrease in the concentration of hemoglobin with respect to boronate moiety binding is obtained in the second detection chamber 200. Moreover, absorbance At of the total hemoglobin (i.e., without any decrease) is determined in the third detection (i.e., control) chamber 210.

As described below, a ratio of difference between absorbance At in the third detection chamber 210 and absorbance A1 in the first detection chamber 190 relative to absorbance At in the third detection chamber 210 or, alternatively, a ratio of difference between absorbance At in the third detection chamber 210 and absorbance A2 in the second detection chamber 200 relative to absorbance At in the third detection chamber 210 is applied to a standard calibration curve (FIG. 4 or 5), which in turn indicates a percentage of HbA1c in the total hemoglobin (i.e., glycated hemoglobin+non-glycated hemoglobin).

Meanwhile, in consideration of a passage for transportation of a fluid by centrifugal force, in one embodiment, the chambers of the micro-fluidic structure are arranged in the rotational body such a way that the sample chambers, the receiving chambers, and the detection chambers are aligned radially, from the center axis of the rotation body toward the circumference, as shown in FIG. 1 and FIG. 2.

According to another aspect of the present invention, there is provided a method for measuring HbA1c using a centrifugal type micro-fluidic device, including providing a micro-fluidic device which includes a first reaction chamber containing an immobilized anti-glycated hemoglobin antibody, a second reaction chamber containing an immobilized boronic acid compound which is capable of binding to a cis-diol group in glycated hemoglobin, and a third reaction chamber which is free of the immobilized anti-glycated hemoglobin antibody and of the immobilized boronic acid compound; bringing an equal volume of a hemolyzed blood sample to be in contact with the immobilized anti-glycated hemoglobin antibody in the first reaction chamber and with the immobilized boronic acid compound in the second reaction chamber, respectively, for a sufficient time to allow the immobilized anti-glycated hemoglobin antibody and the immobilized boronic acid compound can bind to glycated hemoglobin in the hemolyzed blood sample; separating the bound glycated hemoglobin from the hemolyzed blood sample to provide a first supernatant of the hemolyzed blood sample from which the glycated hemoglobin bound to the anti-glycated hemoglobin antibody is removed and a second supernatant of the hemolyzed blood sample from which the glycated hemoglobin bound to the boronic acid compound is removed; measuring absorbance of the first supernatant, the second supernatant, and a unreacted hemolyzed blood sample, respectively; calculating a first absorbance ratio with respect to the first supernatant according to the following Equation 1, and obtaining a first HbA1c level (%) from a standard calibration curve with respect to the glycated hemoglobin bound to the antibody; calculating a second absorbance ratio with respect to the second supernatant according to the following Equation 2, and obtaining a second HbA1c level (%) from a standard calibration curve with respect to the glycated hemoglobin bound to the boronate compound; and comparing the first HbA1c level (%) with the second HbA1c level (%), first absorbance ratio={(absorbance of unreacted hemolyzed blood sample−absorbance of first supernatant)/absorbance of unreacted hemolyzed blood sample}, and   Equation 1:

second absorbance ratio={(absorbance of unreacted hemolyzed blood sample−absorbance of second supernatant)/absorbance of unreacted hemolyzed blood sample}.   Equation 2:

The foregoing method may further include a washing process for removal of unreacted and/or non-reactive materials between respective steps described above.

Hereinafter, a method for measuring HbA1c using the foregoing micro-fluidic device will be described in detail.

<Introduction of Sample>

Analytic buffers and a washing solution are loaded beforehand into the micro-fluidic device according to the present embodiment. That is, a buffer chamber 120 contains a red blood cell lysis buffer for hemolysis of a blood sample. A washing solution chamber (not shown) contains a washing solution. Also, a first chamber 130 contains first HbA1c affinitive particles wherein an antibody selectively binding to HbA1c is fixed to a surface of the particles, while a second chamber 140 contains second HbA1c affinitive particles wherein a boronate moiety (collectively referred to as "boronic acid compound") such as boronic acid, boronate or a boronate derivative binding to a cis-diol group of HbA1c is fixed to a surface of the particles. If each of such first and second HbA1c affinitive particles is present in a liquid state, a concentration thereof ranges from 0.01 to 10 wt. %. The particles to which an antibody or boronate moiety is immobilized may be selected from the group consisting of a spherical, a planar, or an undulating surface and irregular forms thereof and the spherical surface is selected from the group consisting of a bead, a rhombus or irregular shapes thereof. The bead can have a size of at least 0.5 to 100 μm. As discussed, the particles may be subjected to surface treatment using a known method to increase its hydrophilicity.

In order to measure HbA1c, an amount as small as 5 to 20 μl of whole blood may be used. A blood sample taken from a subject is loaded into a sample chamber 110 of the micro-fluidic device.

<Hemolysis>

Rotating the micro-fluidic device, the blood sample is transported from the sample chamber 110 to the buffer chamber 120. The blood sample is hemolyzed by the red blood cell lysis buffer solution contained in the buffer chamber 120. In this case, rotating or vertically shaking the micro-fluidic device may facilitate a homogeneous mixing of the blood sample with the buffer solution.

<Transportation of Blood Sample to the Receiving Chamber and the Control Chamber>

By rotating the micro-fluidic device, the hemolyzed blood sample in the buffer chamber 120 is transported into the first and second chambers 130 and 140 as well as the control chamber 150.

The hemolyzed blood sample of a precisely measured amount (a pre-metered volume) is loaded into the first and second chambers 130 and 140 as well as the control chamber 150. For this purpose, control parameters such as a diameter and/or length of each channel between the buffer chamber 110 and the first and second chambers 130 and 140 as well as the control chamber 150 may be adjusted in order to load the blood sample in an equal amount to each of the chambers, as described above. Otherwise, a pre-metered volume of the blood sample is introduced through each metering chamber 300, 310 or 320 placed at the midst of each channel between the buffer chamber 110 and each of the first and second chambers 130 and 140 as well as the control chamber 150, as shown in FIG. 2.

<Coupling Reaction>

The hemolyzed blood sample which was transported from the buffer chamber to the first and second chambers 130 and 140 is brought to be in contact with the first and second HbA1c affinitive particles contained in the chambers 130 and 140, respectively.

Rotating the micro-fluidic device may facilitate the hemolyzed blood sample to be mixed with the HbA1c affinitive particles. HbA1c affinitive particles in the first chamber 130, which contain an antibody immobilized onto a surface of the particles wherein the antibody selectively binds to HbA1c, are mixed with the hemolyzed blood sample which is tested for HbA1c. HbA1c affinitive particles in the second chamber 140, which contain a boronate moiety such as boronic acid, boronate or a boronate derivative immobilized onto the particles, are mixed for 3 to 15 minutes at a specific temperature selected from 25-37 degree Celsius with the hemolyzed blood sample which is tested for HbA1c.

<Precipitation>

After of the above step that the HbA1c in the hemolyzed blood sample is coupled to affinitive particles in the first and second chambers 130 and 140, respectively, the valves 240 and 250 are opened. By rotation of the micro-fluidic device, a complex of HbA1c affinitive particles with HbA1c in each of the first and second chambers 130 and 140 is allowed to precipitate into each of the first and second sedimentation chambers 160 and 170. As described above, since the HbA1c affinitive particles are coupled to a solid phase having a specific gravity sufficient to enable a homogenous mixing of HbA1c particles with the hemolyzed blood sample and precipitation of the resulting complexes of HbA1c and particles under centrifugal force, the resulting complexes are easily separated from the hemolyzed blood and precipitated into each of the first and second sedimentation chambers 160 and 170 by rotation of the micro-fluidic device.

When opening the valves 240 and 250, the valve 260 may open at the same time. Since a same centrifugal force is applied to the control chamber 150, and the first and second chambers 130 and 140, blood components having a larger specific gravity than hemoglobin, such as white blood cells, present in the hemolyzed blood sample in the control chamber 150 may also be precipitated into the third sedimentation chamber 180. This allows an enhanced precise measurement of absorbance of the total hemoglobin (hemoglobin plus glycated hemoglobin), as described below.

<Detection>

After completing precipitation, the valves 270 to 290 are opened and the micro-fluidic device is rotated.

As a result, each supernatant remaining in the first and second chambers 130 and 140 as well as the control chamber 150 is transported into the first to third detection chambers 190, 200 and 210. Using an appropriate detector, absorbance of hemoglobin in each of the detection chambers 190 to 210 is measured. A detection unit, that is, the detector may be a known optical system for determining absorbance. For example, an optical system comprising monochromatic light emitting photodiodes and LEDs may be used. Here, using light with a wavelength of 400 to 600 nm at which hemoglobin-specific light absorption is observed, the absorbance of hemoglobin may be measured. FIG. 3 is a graph showing molar extinction coefficient (wavelength) of hemoglobin.

Hereinbefore, a process where the immobilized antibody and immobilized boronic acid compound are coupled to a particle and the bound HbA1c (i.e., HbA1c bound to the particles onto which the antibody or the boronic acid compound are immobilized) are precipitated in a detection is explained. In another embodiment, the antibody and boronic acid compound may be immobilized to an inner surface of the chamber and bound HbA1c remains in the chamber and a supernatant alone may be moved to a detection chamber for determining absorbance. In the other embodiment, the antibody and boronic acid compound may be immobilized to a surface of the particle having diameter greater than the inner diameter of outlet channel and bound HbA1c remains in the chamber and a supernatant alone may be moved to a detection chamber for determining absorbance.

Figure 6:
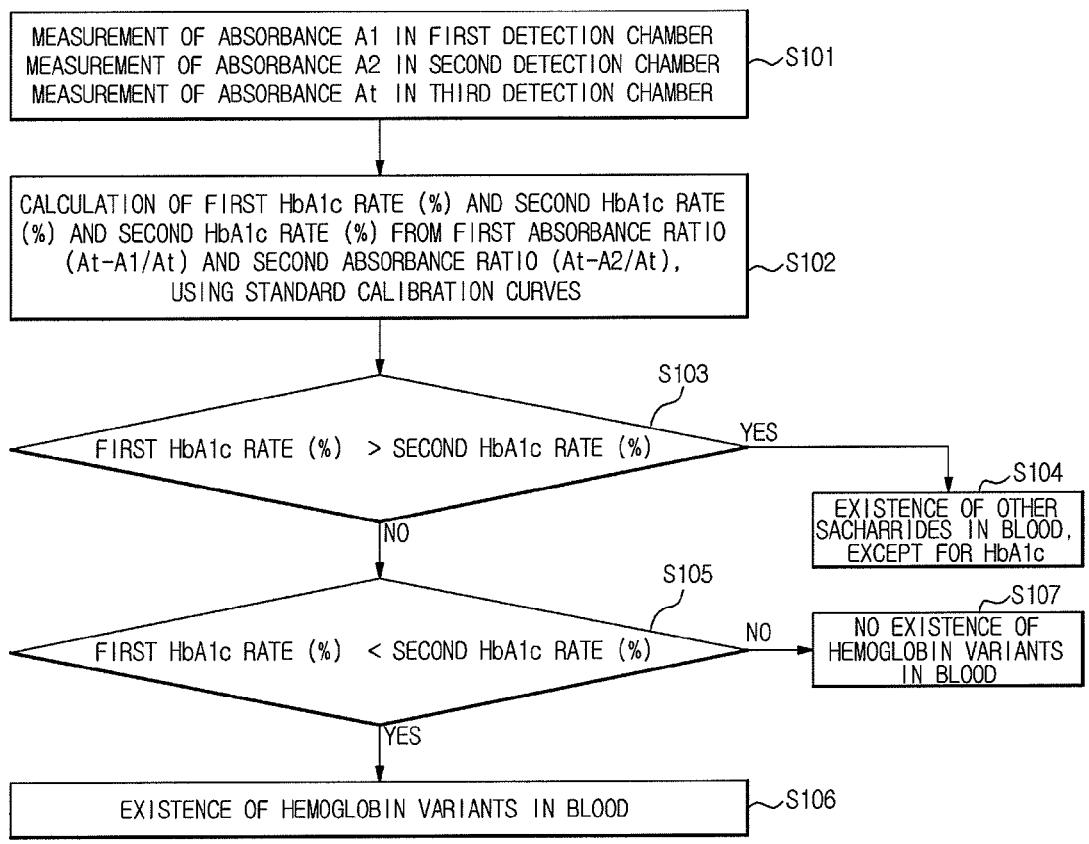
FIG. 6 is a block diagram partially explaining a method for measurement of HbA1c (%).

FIG. 6 is a block diagram partially explaining a method of determining HbA1c.

In the first and second detection chambers 190 and 200, a decrease in the concentration of hemoglobin caused by precipitating the HbA1c bound to HbA1c affinitive particles is optically determined.

Therefore, absorbance A1 indicating a decrease in the concentration of hemoglobin with respect to antibody affinity may be measured in the first detection chamber 190, while absorbance A2 indicating a decrease in concentration of hemoglobin with respect to boronate affinity may be measured in the second detection chamber 200. Moreover, absorbance At of whole hemoglobin is obtained from the third detection chamber 210 (Step S101).

Using a standard calibration curve, a percentage of HbA1c may be determined by applying a ratio of difference (At−A1) between absorbance At in the third detection chamber 210 and absorbance A1 of reduced hemoglobin in the first detection chamber 190, which was decreased relative to absorbance At in the third detection chamber 210, and/or a ratio of difference (At−A2) between absorbance At in the third detection chamber 210 and absorbance A2 of reduced hemoglobin in the second detection chamber 200, which was decreased relative to absorbance At in the third detection chamber 210.

Figure 4:
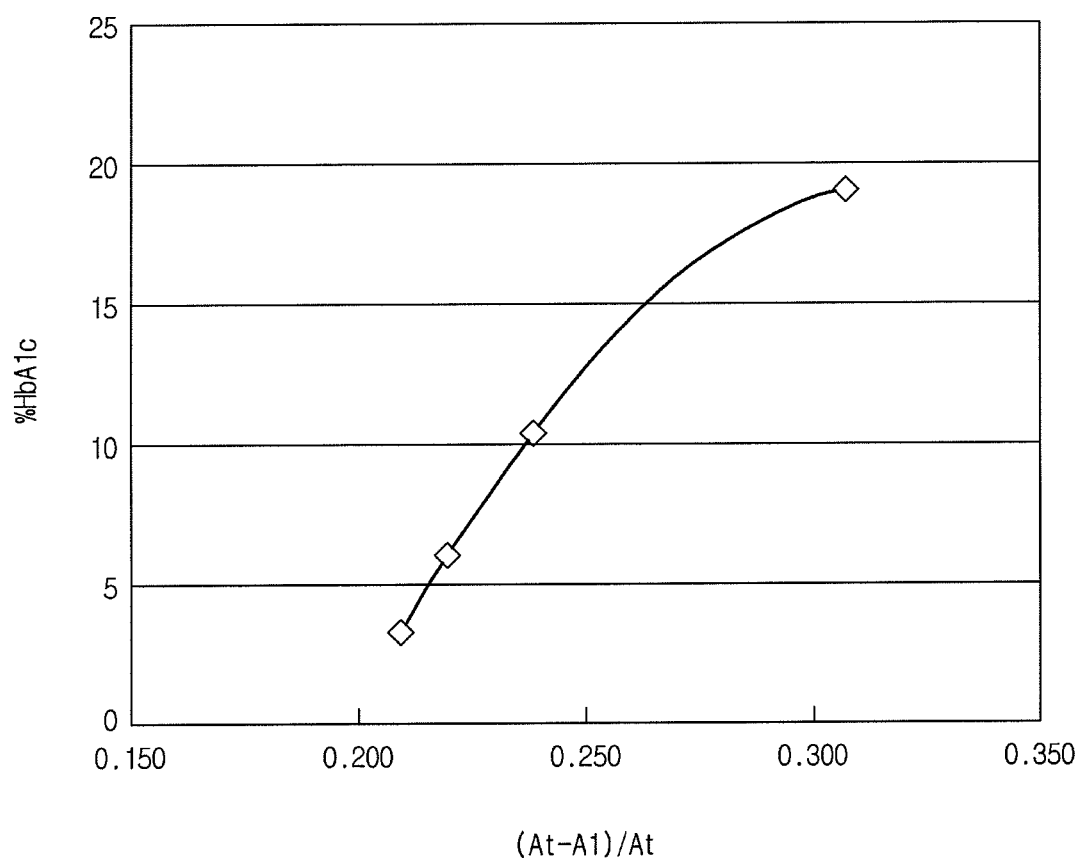
FIG. 4 is a standard calibration curve obtained with respect to an antibody, wherein x axis indicates a ratio of [absorbance of whole hemoglobin (At)−absorbance with reduced concentration of hemoglobin (A1)]/absorbance of whole hemoglobin (At) with respect to antibody and y axis represents HbA1c (%)

FIG. 4 shows a standard calibration curve obtained with respect to antibody wherein x axis indicates a ratio of [absorbance of total hemoglobin (At)−absorbance with reduced concentration of hemoglobin (A1)]/absorbance of total hemoglobin (At) with respect to antibody and y axis represents HbA1c (%). Likewise, FIG. 5 is a standard calibration curve obtained with respect to boronate affinity wherein x axis indicates a ratio of [absorbance of total hemoglobin (At)−absorbance with reduced concentration of hemoglobin (A2)]/absorbance of total hemoglobin (At) with respect to boronate affinity and y axis represents HbA1c (%).

Figure 5:
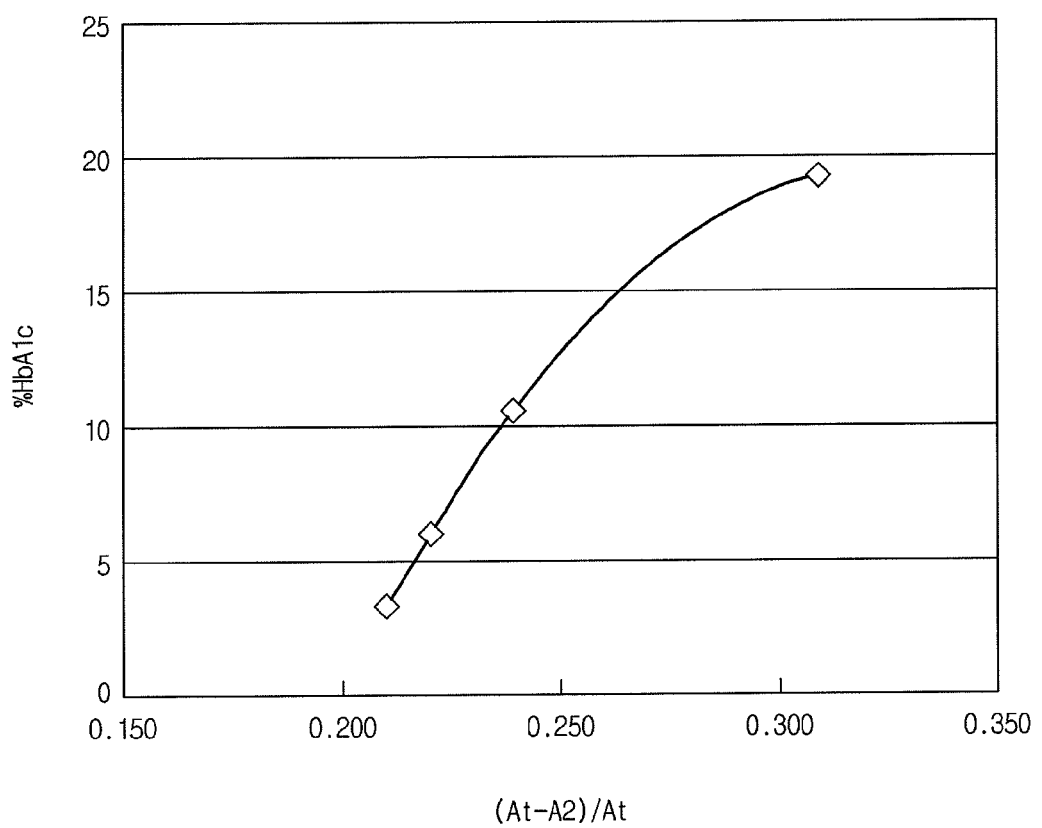
FIG. 5 is a standard calibration curve obtained with respect to boronate affinity, wherein x axis indicates a ratio of [absorbance of whole hemoglobin (At)−absorbance with reduced concentration of hemoglobin (A2)]/absorbance of whole hemoglobin (At) with respect to boronate affinity and y axis represents HbA1c (%)

When substituting (At−A1)/At ratio and (At−A2)/At ratio into the standard calibration curves shown in FIGS. 4 and 5, respectively, the HbA1c level (%) may be calculated.

The following description will be given of an illustrative embodiment for calculation of HbA1 level (%) by preparing the standard calibration curve of FIG. 4 and using the prepared calibration curve.

After loading several blood samples with known HbA1c level into the sample chamber 110, absorbance in each of the first and third detection chambers 190 and 210 with respect to antibody was determined according to the foregoing method. In the present embodiment, a total of four blood samples were used to determine absorbance in each of the first and third detection chambers 190 and 210.

As shown in the following Table 1, (At−A1)/At may be measured.

TABLE 1

| | HbA1c (%) | At | A1 | At − A1/At | Result of HbA1c (%) | Recovery |
|---|---|---|---|---|---|---|
| 1 | 19.1 | 2.529 | 1.753 | 0.307 | 19.1 | 100% |
| 2 | 10.4 | 2.414 | 1.840 | 0.238 | 10.4 | 100% |
| 3 | 6.0 | 3.093 | 2.141 | 0.220 | 6.0 | 100% |
| 4 | 3.3 | 3.117 | 2.464 | 0.210 | 3.3 | 100% |
| 5 | Unknown | 2.776 | 2.154 | 0.224 | 7.2 | |

With results of Nos. 1 to 4 in TABLE 1, the standard calibration curve shown in FIG. 4 may be plotted.

After loading a blood sample with unknown HbA1c concentration into the sample chamber 110, absorbance A1 in the detection chamber 190 and absorbance At in the third detection chamber 210 were measured using the prepared standard calibration curve according to the foregoing method and (At−

A1)/At was calculated. Then, substituting the calculated value into the same calibration curve, HbA1c with respect to antibody was finally obtained. In the present embodiment, (At−A1)/At was 0.224 and, applying this value to the calibration curve shown in FIG. 4, 7.0% HbA1c was finally calculated.

In the same way, absorbance in each of the second and third detection chambers 200 and 210 was measured and a HbA1c level with respect to boronate moiety affinity was calculated using the standard calibration curve shown in FIG. 5.

The first HbA1c level (%) with respect to antibody and the second HbA1c level (%) with respect to boronate moiety affinity were compared with each other.

If the blood sample contains a material receiving cis-diol groups, the first HbA1c level (%) is higher than the second HbA1c level (%). On the other hand, when hemoglobin variants are present in the blood sample, the first HbA1c level (%) is less than the second HbA1c level (%).

TABLE 2

| | First HbA1c % > second HbA1c % | First HbA1c % = second HbA1c % | First HbA1c % < second HbA1c % |
|---|---|---|---|
| Existence of variants | Interfering substances receiving cis-diol groups in blood sample | Normal | Hemoglobin variants in blood sample |

As listed in TABLE 2, if the blood sample contains a material receiving cis-diol groups, the first HbA1c level (%) is higher than the second HbA1c level (%). On the other hand, when hemoglobin variants are present in the blood sample, the first HbA1c level (%) is less than the second HbA1c level (%).

As a result of comparison between the first HbA1c level (%) and the second HbA1c level (%), it can be determined whether interfering substances receiving cis-diol groups and/or hemoglobin variants exist in the blood sample.

In case where the first HbA1c level (%) is higher than the second HbA1c level (%) ('Yes' in S103), it may be determined that interfering substances such as saccharides other than HbA1c are present in the blood sample (S104). On the contrary, if the first HbA1c level (%) is lower than the second HbA1c level (%) ('Yes' in S105), it may be determined that hemoglobin variants are present in the blood sample (S106). Such determined results are provided to an experimenter who may further take appropriate measures as appropriate.

In case where the first HbA1c level (%) is substantially identical to the second HbA1c level (%) or a difference therebetween is not significant ('No' in S105), it is determined that the blood sample does not contain hemoglobin variants (S107).

Evaluation criteria for a significant difference between both the first and second HbA1c levels may be statically defined through critical trials, including reflection of inherent characteristics of individual groups such as race, region, etc.

Consequently, the foregoing method may not only calculate HbA1c level (%) with respect to antibody and HbA1c level (%) with respect to boronate affinity, but also provide information for existence of hemoglobin variants and/or interfering substances such as saccharides, which may interfere with an accurate measurement of HbA1c, in a blood sample. If such hemoglobin variants or interfering substances are present in the blood sample, the experimenter may conduct further analysis such as HLPC based on the foregoing information so as to determine an accurate and precise HbA1c level (%). On the contrary, when experimental results demonstrate no existence of hemoglobin variants/interfering substances, the HbA1c level (%) measured according to the above method may be defined as the percentage of glycated hemoglobin.

Although a few embodiments of the present invention have been shown and described, it would be appreciated by those skilled in the art that substitutions, variations and/or modifications may be made in these embodiments without departing from the principles and spirit of the invention, the scope of which is defined in the claims and their equivalents.

What is claimed is:

1. A centrifugal micro-fluidic structure, comprising:
   a plurality of chambers;
   channels through which the chambers are connected to one another; and
   valves for opening and closing the channels,
   wherein the plurality of chambers include a first reaction chamber comprising a first material which has a first affinity to glycated hemoglobin; a second reaction chamber comprising a second material which has a second affinity to glycated hemoglobin, said second affinity being different from the first affinity; and a third reaction chamber which is free of the first material and the second material and is served as a control chamber, and
   wherein the plurality of chambers are connected such that a first sample that passes through the first reaction chamber does not pass through either of the second reaction chamber and the third reaction chamber, a second sample that passes through the second reaction chamber does not pass through either of the first reaction chamber and the third reaction chamber, and a third sample that passes through the third reaction chamber does not pass through either of the first reaction chamber and the second reaction chamber.

2. The centrifugal micro-fluidic structure according to claim 1, wherein the first material is an anti-glycated hemoglobin antibody; and the second material is a boronic acid compound which is capable of binding to a cis-diol group of glycated hemoglobin.

3. The centrifugal micro-fluidic structure according to claim 1, wherein the first material is immobilized to a particle and the second material are immobilized to a particle.

4. The centrifugal micro-fluidic structure according to claim 1, wherein the first material is immobilized onto an inner surface of the first chamber and the second material is immobilized onto an inner surface of the second chamber.

5. The centrifugal micro-fluidic structure according to claim 3, wherein the particles are solid support having a specific gravity of 1.3-2.0.

6. The centrifugal micro-fluidic structure according to claim 3, wherein the antibody is a monoclonal antibody or a polyclonal antibody.

7. The centrifugal micro-fluidic structure according to claim 3, further including
   a first sedimentation chamber to receive glycated hemoglobin bound to the particle to which the first material is immobilized; and
   a second sedimentation chamber to receive glycated hemoglobin bound to the particle to which the second material is immobilized.

8. The centrifugal micro-fluidic structure according to claim 5, further including
   a first sedimentation chamber to receive glycated hemoglobin bound to the particle to which the first material is immobilized; and a second sedimentation chamber to receive glycated hemoglobin bound to the particle to which the second material is immobilized.

9. The centrifugal micro-fluidic structure according to claim 1, further comprising
a first detection chamber to receive a supernatant of a test sample from which the glycated hemoglobin bound to the first material is separated;
a second detection chamber to receive a supernatant of the test sample from which the glycated hemoglobin bound to the second material is separated; and
a third detection chamber to receive a supernatant of the test sample from the third reaction chamber.

10. The centrifugal micro-fluidic structure according to claim 9, wherein the first, the second, and the third reaction chambers are arranged to have an equal distance from the rotation axis of the centrifugal micro-fluidic structure; wherein the first, the second, and the third detection chambers are arranged to have an equal distance from the rotation axis of the centrifugal micro-fluidic structure; and wherein the first, the second, and the third detection chambers are placed radially farther from the rotation axis than the first, the second, and the third reaction chambers, respectively.

11. A centrifugal micro-fluidic device, comprising:
a rotational body,
at least one micro-fluidic structure, and
a detection unit,
wherein the micro-fluidic structure is a centrifugal micro-fluidic structure, including:
a plurality of chambers;
channels through which the chambers are connected to one another; and
valves or opening and closing the channels,
wherein the plurality of chambers include a first reaction chamber comprising a first material which has a first affinity to glycated hemoglobin; a second reaction chamber comprising a second material which has a second affinity to glycated hemoglobin, said second affinity being different from the first affinity; and a third reaction chamber which is free of the first material and the second material and is served as a control chamber;
wherein a fluid contained in the micro-fluidic structure is transported using centrifugal force generated by rotation of the rotational body; and
wherein the plurality of chambers are connected such that a first sample that passes through the first reaction chamber does not pass through either of the second reaction chamber and the third reaction chamber, a second sample that passes through the second reaction chamber does not pass through either of the first reaction chamber and the third reaction chamber, and a third sample that passes through the third reaction chamber does not pass through either of the first reaction chamber and the second reaction chamber.

12. The centrifugal micro-fluidic device according to claim 9, wherein the detection unit has an optical system emitting monochromatic light and the optical system measures absorbance of each of first to third detection chambers using light with a wavelength ranging from 400 to 600 nm.

13. The centrifugal micro-fluidic structure according to claim 1, further comprising a sample chamber in which a sample is loaded, and which provides, as the first sample, a portion of the loaded sample to the first reaction chamber and provides, as the second sample, another portion of the loaded sample to the second reaction chamber.

* * * * *